(12) United States Patent
O'Donnell et al.

(10) Patent No.: US 11,617,844 B2
(45) Date of Patent: Apr. 4, 2023

(54) FLOW PATH FAULT DETECTION METHOD FOR A RESPIRATORY ASSISTANCE APPARATUS

(71) Applicant: Fisher & Paykel Healthcare Limited, Auckland (NZ)

(72) Inventors: Kevin Peter O'Donnell, Auckland (NZ); John Han, Auckland (NZ); Jack Che-Wei Hsu, Auckland (NZ); Samuel Robertson Frame, Auckland (NZ); Grant Martin Dover, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 747 days.

(21) Appl. No.: 16/518,827

(22) Filed: Jul. 22, 2019

(65) Prior Publication Data

US 2019/0336711 A1    Nov. 7, 2019

Related U.S. Application Data

(62) Division of application No. 14/402,583, filed as application No. PCT/NZ2013/000088 on May 23, 2013, now Pat. No. 10,398,861.

(Continued)

(51) Int. Cl.
  *A61M 16/00*     (2006.01)
  *A61M 16/16*     (2006.01)
  *A61M 16/10*     (2006.01)

(52) U.S. Cl.
  CPC ...... *A61M 16/0051* (2013.01); *A61M 16/024* (2017.08); *A61M 16/16* (2013.01);
  (Continued)

(58) Field of Classification Search
  CPC .......... A61M 16/0003; A61M 16/0051; A61M 16/0066; A61M 16/022; A61M 16/024;
  (Continued)

(56) References Cited

U.S. PATENT DOCUMENTS 5,203,343 A   4/1993  Axe et al.
5,551,419 A   9/1996  Froehlich et al.
(Continued)

FOREIGN PATENT DOCUMENTS

AU   7197898 A  * 12/1998
EP   0661071 B1   2/2000
(Continued)

OTHER PUBLICATIONS

International Search Report; PCT/NZ2013/000088; dated Aug. 9, 2013; 4 pages.

(Continued)

*Primary Examiner* — Kathryn E Ditmer
(74) *Attorney, Agent, or Firm* — Knobbe, Martens, Olson & Bear, LLP

(57) ABSTRACT

A respiratory assistance apparatus is configured to provide a heated and humidified glow of gases and has a control system that is configured to detect a fault in the flow path. A flow path is provided for a gases stream through the apparatus from a gas inlet through a blower unit and humidification unit to a gases outlet. A flow rate sensor is provided in the flow path and is configured to sense the flow rate and generate an flow rate signal and/or a motor speed sensor is provided that is configured to sense the motor speed of the blower unit and generate an indicative motor speed signal.

10 Claims, 11 Drawing Sheets

Related U.S. Application Data

(60) Provisional application No. 61/650,680, filed on May 23, 2012.

(52) U.S. Cl.
CPC ..... *A61M 16/0069* (2014.02); *A61M 16/1095* (2014.02); *A61M 16/161* (2014.02); *A61M 2016/003* (2013.01); *A61M 2016/0039* (2013.01); *A61M 2205/14* (2013.01); *A61M 2205/15* (2013.01); *A61M 2205/18* (2013.01); *A61M 2205/3334* (2013.01); *A61M 2205/3365* (2013.01); *A61M 2205/3368* (2013.01); *A61M 2205/502* (2013.01); *A61M 2205/52* (2013.01); *A61M 2205/70* (2013.01); *A61M 2205/705* (2013.01); *A61M 2205/707* (2013.01)

(58) Field of Classification Search
CPC .............. A61M 16/04; A61M 16/0666; A61M 16/109; A61M 16/16
See application file for complete search history.

(56) References Cited

U.S. PATENT DOCUMENTS

| | | | |
|---|---|---|---|
| 6,240,921 B1 | 6/2001 | Brydon et al. | |
| 6,360,741 B2 | 3/2002 | Truschel | |
| 6,536,432 B2 | 3/2003 | Truschel | |
| 7,987,847 B2 | 8/2011 | Wickham | |
| 8,069,854 B2 | 12/2011 | Colla et al. | |
| 2001/0004894 A1 | 6/2001 | Bourdon | |
| 2003/0111079 A1* | 6/2003 | Matthews | A61M 16/026 128/204.18 |
| 2005/0076906 A1 | 4/2005 | Johnson | |
| 2006/0086357 A1* | 4/2006 | Soliman | A61M 16/0051 128/204.22 |
| 2007/0221224 A1 | 9/2007 | Pittman et al. | |
| 2008/0251071 A1 | 10/2008 | Armitstead et al. | |
| 2008/0295837 A1 | 12/2008 | McCormick et al. | |
| 2009/0199850 A1* | 8/2009 | Colla | A61M 16/024 128/204.21 |
| 2009/0293875 A1* | 12/2009 | Kwok | A61M 16/024 128/204.18 |
| 2010/0010477 A1 | 1/2010 | Augustine et al. | |
| 2012/0247470 A1 | 10/2012 | Ho et al. | |
| 2013/0312750 A1 | 11/2013 | Farrugia et al. | |
| 2014/0283831 A1 | 9/2014 | Foote et al. | |
| 2015/0144130 A1 | 5/2015 | O'Donnell et al. | |

FOREIGN PATENT DOCUMENTS

| | | | |
|---|---|---|---|
| WO | WO 2006/133494 | 12/2006 | |
| WO | WO 2012/012835 | 2/2012 | |
| WO | WO 2012/020314 | 2/2012 | |
| WO | WO-2012020314 A2 * | 2/2012 | ........... A61B 5/4809 |

OTHER PUBLICATIONS

Written Opinion of the Isa; PCT/NZ2013/00088; dated Aug. 9, 2014; 6 pages.
Office Action in corresponding Canadian Patent Application No. 2,871,850, dated Mar. 12, 2020, in 4 pages.

* cited by examiner

FLOW PATH FAULT DETECTION METHOD FOR A RESPIRATORY ASSISTANCE APPARATUS

FIELD OF THE INVENTION

This invention relates to a flow path fault detection method and system for a respiratory assistance apparatus that provides a stream of heated and humidified gases to a user for therapeutic purposes. In particular, although not exclusively, the respiratory assistance apparatus may provide respiratory assistance to patients or users who require a supply of heated and humidified gases for respiratory therapies such as respiratory humidification therapy, high-flow oxygen therapy, Positive Airway Pressure (PAP) therapies, including CPAP therapy, Bi-PAP therapy, and OPAP therapy, and typically for the treatment of diseases such as Obstructive Sleep Apnea (OSA), snoring, or Chronic Obstructive Pulmonary Disease (COPD).

BACKGROUND TO THE INVENTION

Respiratory assistance devices or systems for providing a flow of humidified and heated gases to a patient for therapeutic purposes are well known in the art. Systems for providing therapy of this type (for example respiratory humidification) typically have a structure where gases are delivered to a humidifier chamber from a gases source, such as a blower (also known as a compressor, an assisted breathing unit, a fan unit, a flow generator or a pressure generator). As the gases pass over the hot water, or through the heated and humidified air in the humidifier chamber, they become saturated with water vapour. The heated and humidified gases are then delivered to a user or patient downstream from the humidifier chamber, via a gases conduit and a user interface.

In one form, such respiratory assistance systems can be modular systems that comprise a humidifier unit and a blower unit that are separate (modular) items. The modules are connected in series via connection conduits to allow gases to pass from the blower unit to the humidifier unit. For example, FIG. 1 shows a schematic view of a user 1 receiving a stream of heated and humidified air from a modular respiratory assistance system. Pressurised air is provided from an assisted breathing unit or blower unit 2a via a connector conduit 10 to a humidifier chamber 4a. The stream of humidified, heated and pressurised air exits the humidification chamber 4a via a user conduit 3, and is provided to the patient or user 1 via a user interface 5.

In an alternative form, the respiratory assistance systems can be integrated systems in which the blower unit and the humidifier unit are contained within the same housing. A typical integrated system consists of a main blower unit or assisted breathing unit which provides a pressurised gases flow, and a humidifier unit that mates with or is otherwise rigidly connected to the blower unit. For example, the humidifier unit is mated to the blower unit by slide-on or push connection, which ensures that the humidifier unit is rigidly connected to and held firmly in place on the main blower unit. FIG. 2 shows a schematic view of the user 1 receiving heated and humidified air from an integrated respiratory assistance system 6. The system operates in the same manner as the modular system shown in FIG. 1, except the humidification chamber 4b has been integrated with the blower unit to form the integrated system 6.

The user interface 5 shown in FIGS. 1 and 2 is a nasal mask, covering the nose of the user 1. However, it should be noted that in systems of these types, a mask that covers the mouth and nose, a full face mask, a nasal cannula, or any other suitable user interface could be substituted for the nasal mask shown. A mouth-only interface or oral mask could also be used. Also, the patient or user end of the conduit can be connected to a tracheostomy fitting, or an endotracheal intubation.

U.S. Pat. No. 7,111,624 includes a detailed description of an integrated system. A 'slide-on' water chamber is connected to a blower unit in use. A variation of this design is a slide-on or clip-on design where the chamber is enclosed inside a portion of the integrated unit in use. An example of this type of design is shown in WO 2004/112873, which describes a blower, or flow generator 50, and an associated humidifier 150.

For these integrated systems, the most common mode of operation is as follows: air is drawn by the blower through an inlet into the casing which surrounds and encloses at least the blower portion of the system. The blower pressurises the air stream from the flow generator outlet and passes this into the humidifier chamber. The air stream is heated and humidified in the humidifier chamber, and exits the humidifier chamber via an outlet. A flexible hose or conduit is connected either directly or indirectly to the humidifier outlet, and the heated, humidified gases are passed to a user via the conduit. This is shown schematically in FIG. 2.

In both modular and integrated systems, the gases provided by the blower unit are generally sourced from the surrounding atmosphere. However, some forms of these systems may be configured to allow a supplementary gas to be blended with the atmospheric air for particular therapies. In such systems, a gases conduit supplying the supplemental gas is typically either connected directly to the humidifier chamber or elsewhere on the high pressure (flow outlet) side of the blower unit, or alternatively to the inlet side of the blower unit as described in WO 2007/004898. This type of respiratory assistance system is generally used where a patient or user requires oxygen therapy, with the oxygen being supplied from a central gases source. The oxygen from the gases source is blended with the atmospheric air to increase the oxygen fraction before delivery to the patient. Such systems enable oxygen therapy to be combined with high flow humidification therapy for the treatment of diseases such as COPD.

The blower unit typically comprises a fan or impeller that is rotatably driven by a variable speed motor and the respiratory assistance system typically further comprises an electronic controller that is configured to control the motor speed of the blower unit to generate a desired flow rate, for example in high flow humidification therapy, based on input from a user input interface. Correct operation of the respiratory assistance system requires an intact flow path from gases inlet of the system to the user interface. Typically, manual observation of the connected components in the flow path is used to determine if any such flow path faults exist and require remedy.

In this specification, where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

It is an object of the present invention to provide an improved method of detecting a fault in the flow path of an respiratory assistance apparatus, or to at least provide the public with a useful choice.

SUMMARY OF THE INVENTION

In broad terms, in a first aspect, the invention comprises a method for detecting a fault in the flow path of a respiratory assistance apparatus, the flow path comprising a motor-driven blower unit that is configured to generate a flow of gases and which is connected to a humidification unit that is configured to heat and humidify the flow of gases, comprising:

sensing the flow rate in the flow path at a first motor speed of the blower unit; detecting if the sensed flow rate exceeds a stored first threshold at the first motor speed; increasing the motor speed of the blower unit to a higher second motor speed if the first threshold is exceeded;

re-sensing the flow rate in the flow path at the second motor speed; and generating a fault detection signal if the re-sensed flow rate at the second motor speed exceeds a stored second threshold.

In some embodiments, the first motor speed is within a first predetermined motor speed range and the second motor speed is within a predetermined second motor speed range. In some embodiments, the first motor speed range comprises the motor speeds required to generate a sensed flow rate in the flow path of below 25 L/min and the second motor speed range comprises the motor speeds required to generate a sensed flow rate in the flow path of at or above 25 L/min.

In some embodiments, the first motor speed is below 6500 rpm.

In some embodiments, the higher second motor speed is at or above 6500 rpm.

In some embodiments, the higher second motor speed is at least 6000 rpm when the respiratory apparatus is operating in an adult mode and delivering the flow of gases to a user via an adult cannula. In some embodiments, the higher second motor speed is at least 4000 rpm when the respiratory apparatus is operating in a junior mode and delivering the flow of gases to a user via a pediatric cannula.

In some embodiments, the first motor speed is the current operating motor speed of the respiratory assistance apparatus. In other embodiments, the method further comprises changing the current operating motor speed to the first motor speed prior to sensing the flow rate.

Preferably, the humidification unit comprises a humidification chamber and sensing the flow rate comprises sensing the flow rate in the flow path prior to the humidification chamber.

In some embodiments, the flow rate is sensed in the flow path prior to the blower unit.

In broad terms, in a second aspect, the invention comprises a method for detecting a fault in the flow path of a respiratory assistance apparatus, the flow path comprising a motor-driven blower unit that is configured to generate a flow of gases and which is connected to a humidification unit that is configured to heat and humidify the flow of gases, comprising:

determining the motor speed of the blower unit required to generate a first set flow rate in the flow path; detecting if the motor speed falls below a stored first threshold at the first set flow rate; increasing the flow rate to a higher second set flow rate if the motor speed falls below the first threshold; re-determining the motor speed of the blower unit required to generate the second set flow rate in the flow path; and generating a fault detection signal if the re-determined motor speed at the second set flow rate falls below a stored second threshold.

In some embodiments, the first set flow rate is within a first predetermined flow rate range and the second set flow rate is within a predetermined second flow rate range. In some embodiments, the first set flow rate range comprises flow rates below 25 L/min and wherein the second set flow rate range comprises flow rates at or above 25 L/min.

In some embodiments, the first set flow rate is the current operating flow of the respiratory assistance apparatus. In other embodiments, the method further comprises changing the current set flow rate of the respiratory assistance apparatus to the first set flow rate prior to determining the motor speed.

In broad terms, in a third aspect, the invention comprises a method for detecting a fault in the flow path of a respiratory assistance apparatus, the flow path comprising a motor-driven blower unit that is configured to generate a flow of gases and which is connected to a humidification unit that is configured to heat and humidify the flow of gases, comprising:

determining the motor speed of the blower unit required to generate a first set flow rate in the flow path; detecting if the motor speed falls below a stored first threshold at the first set flow rate; increasing the motor speed of the blower unit to a higher motor speed if the determined motor speed falls below the first threshold; sensing the flow rate in the flow path at the higher motor speed; and generating a fault detection signal if the sensed flow rate at the higher motor speed exceeds a stored second threshold.

In some embodiments, the first set flow rate is in a flow rate range below 25 L/min and wherein the higher motor speed is in a motor speed range comprising motor speeds required to generate a sensed flow rate in the flow path at or above 25 L/min.

In some embodiments, the higher motor speed is at or above 6500 rpm.

In some embodiments, the higher motor speed is at least 6000 rpm when the respiratory apparatus is operating in an adult mode and delivering the flow of gases to a user via an adult cannula. In some embodiments, the higher motor speed is at least 4000 rpm when the respiratory apparatus is operating in a junior mode and delivering the flow of gases to a user via a pediatric cannula.

In some embodiments, the first set flow rate is the current operating flow of the respiratory assistance apparatus. In other embodiments, the method further comprises changing the current set flow rate of the respiratory assistance apparatus to the first set flow rate prior to determining the motor speed.

Preferably, the humidification unit comprises a humidification chamber and sensing the flow rate comprises sensing the flow rate in the flow path prior to the humidification chamber. In some embodiments, the flow rate is sensed in the flow path prior to the blower unit.

In broad terms, in a fourth aspect, the invention comprises a method for detecting a fault in the flow path of a respiratory assistance apparatus, the flow path comprising a motor-driven blower unit that is configured to generate a flow of gases and which is connected to a humidification unit that is configured to heat and humidify the flow of gases, comprising:

sensing the flow rate in the flow path at a first motor speed of the blower unit; detecting if the sensed flow rate exceeds a stored first threshold at the first motor speed; increasing the flow rate to a higher set flow rate if the sensed flow rate exceeds the first threshold; determining the motor speed of the blower unit required to generate the higher set flow rate in the flow path; and generating a fault detection signal if the determined motor speed at the higher set flow rate falls below a stored second threshold.

In some embodiments, the first motor speed is in a motor speed range comprising motor speeds required to generate a sensed flow rate in the flow path of below 25 L/min and wherein the higher set flow rate comprises flow rates at or above 25 L/min.

In some embodiments, the first motor speed is below 6500 rpm.

In some embodiments, the first motor speed is the current operating motor speed of the respiratory assistance apparatus. In other embodiments, the method further comprises changing the current operating motor speed to the first motor speed prior to sensing the flow rate.

Preferably, the humidification unit comprises a humidification chamber and sensing the flow rate comprises sensing the flow rate in the flow path prior to the humidification chamber. In some embodiments, the flow rate is sensed in the flow path prior to the blower unit.

The following features may apply to any one or more of the above aspects of the invention.

In at least some embodiments, the first threshold has a higher probability of false alarm compared to the second threshold.

In at least some embodiments, the first and second thresholds are discrete stored values.

In at least some embodiments, the first and second thresholds are extracted from respective stored threshold lines representing the flow rate threshold against motor speed for a predetermined motor speed range, and/or stored threshold lines representing the motor speed threshold against set flow rates for a predetermined flow rate range.

In at least some embodiments, the first and second thresholds are configured for detecting the removal of a humidification chamber from the humidification unit in the flow path such that the fault detection signal is indicative of disconnection or removal of the humidification chamber from the flow path.

In at least some embodiments, the first and second thresholds are configured for detecting a leak in the flow path such that the fault detection signal is indicative of detected leak in the flow path.

In at least some embodiments, the method further comprises adjusting the first threshold by a predetermined level if the fault detection signal is not generated. Preferably, adjusting the first threshold comprises limiting the first threshold to a limit level.

In at least some embodiments, the method further comprises triggering an alarm if the fault detection signal is generated.

In broad terms, in a fifth aspect, the invention comprises a method for detecting a fault in the flow path of a respiratory assistance apparatus, the flow path comprising a motor-driven blower unit that is configured to generate a flow of gases and which is connected to a humidification unit that is configured to heat and humidify the flow of gases, comprising:

sensing the flow rate in the flow path at a first motor speed of the blower unit; detecting if the sensed flow rate is below a stored first threshold at the first motor speed; increasing the motor speed of the blower unit to a higher second motor speed if the sensed flow rate is below the first threshold; re-sensing the flow rate in the flow path at the second motor speed; and generating a fault detection signal if the re-sensed flow rate at the second motor speed is below a stored second threshold.

Preferably, the first and second thresholds are configured for detecting a blockage in the flow path such that the fault detection signal is indicative of a detected blockage in the flow path.

In some embodiments, the higher second motor speed is at least 2000 rpm when the respiratory apparatus is operating in an adult mode and delivering the flow of gases to a user via an adult cannula. In some embodiments, the higher second motor speed is at least 6600 rpm when the respiratory apparatus is operating in a junior mode and delivering the flow of gases to a user via a pediatric cannula.

In broad terms, in a sixth aspect, the invention comprises a method for detecting a leak or blockage in the flow path of a respiratory assistance apparatus, the flow path comprising a motor-driven blower unit that is configured to generate a flow of gases and which is connected to a humidification unit that is configured to heat and humidify the flow of gases, comprising: sensing the flow rate in the flow path at a first motor speed of the blower unit;

detecting if the sensed flow rate exceeds a stored first leak threshold at the first motor speed or is below a stored first blockage threshold at the first motor speed; increasing the motor speed of the blower unit to a higher second motor speed if the sensed flow rate exceeds the first leak threshold or is below the first blockage threshold; re-sensing the flow rate in the flow path at the second motor speed; and generating a fault detection signal if the re-sensed flow rate at the second motor speed exceeds a stored second leak threshold or is below a stored second blockage threshold.

In broad terms, in a seventh aspect, the invention comprises respiratory assistance apparatus configured to provide a heated and humidified glow of gases, comprising: a gases inlet configured to receive a supply of gases; a motor-driven blower unit configured to generate a pressurized gases stream from the supply of gases; a humidification unit configured to heat and humidify the pressurized gases stream; a gases outlet for the heated and humidified gases stream; a flow path for the gases stream through the respiratory device from the gas inlet through the blower unit and humidification unit to the gases outlet; a flow rate sensor in the flow path that is configured to sense the flow rate and generate an indicative flow rate signal and/or a motor speed sensor that is configured to sense the motor speed of the blower unit and generate an indicative motor speed signal; and a control system that is configured to detect a fault in the flow path by carrying out the method as defined in any of the aspects of the invention above.

The seventh aspect of the invention may have any one or more of the features mentioned in respect of the first-sixth aspects of the invention.

The term "comprising" as used in this specification and claims means "consisting at least in part of". When interpreting each statement in this specification and claims that includes the term "comprising", features other than that or those prefaced by the term may also be present. Related terms such as "comprise" and "comprises" are to be interpreted in the same manner.

It is intended that reference to a range of numbers disclosed herein (for example, 1 to 10) also incorporates reference to all rational numbers within that range (for example but without limitation, 1, 1.1, 2, 3, 3.9, 4, 5, 6, 6.5, 7, 8, 9 and 10) and also any range of rational numbers within that range (for example but without limitation, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

As used herein, the term "and/or" means "and" or "or", or both.

As used herein, "(s)" following a noun means the plural and/or singular forms of the noun.

The invention consists in the foregoing and also envisages constructions of which the following gives examples only.

BRIEF DESCRIPTION OF THE DRAWINGS

Preferred embodiments of the invention will be described by way of example only and with reference to the drawings, in which.

DETAILED DESCRIPTION OF PREFERRED EMBODIMENTS

Overview

Figure 1:
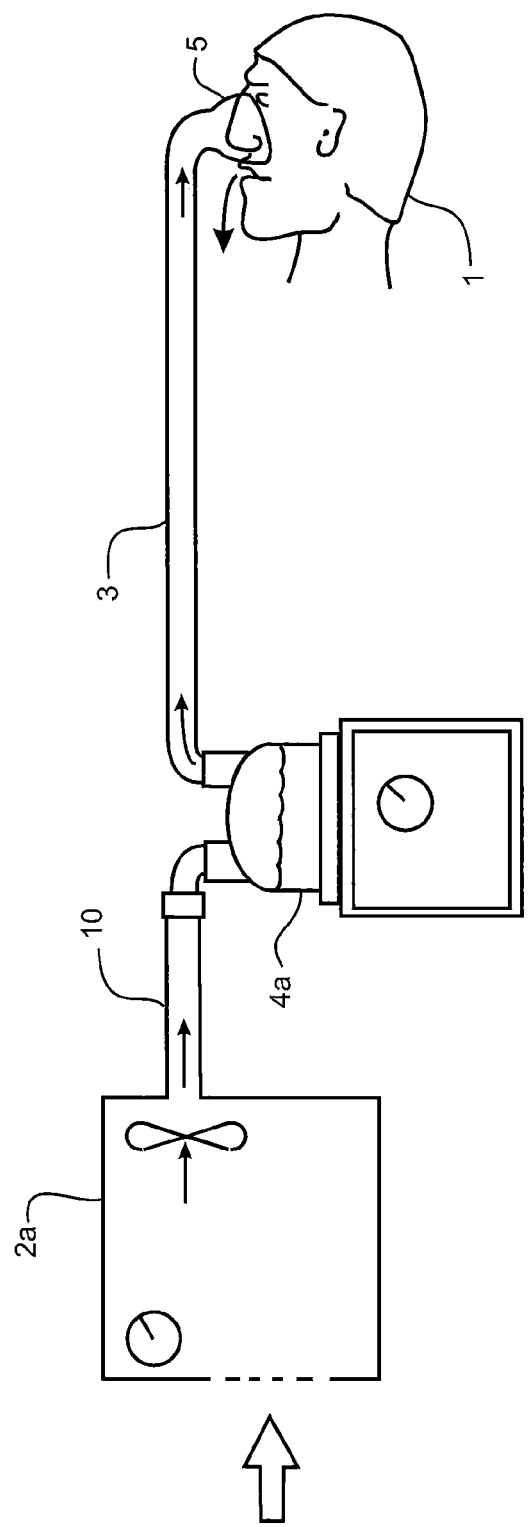
FIG. 1 is a schematic view of a known form of respiratory assistance apparatus having a modular configuration blower unit connected to a humidifier unit.
Figure 2:
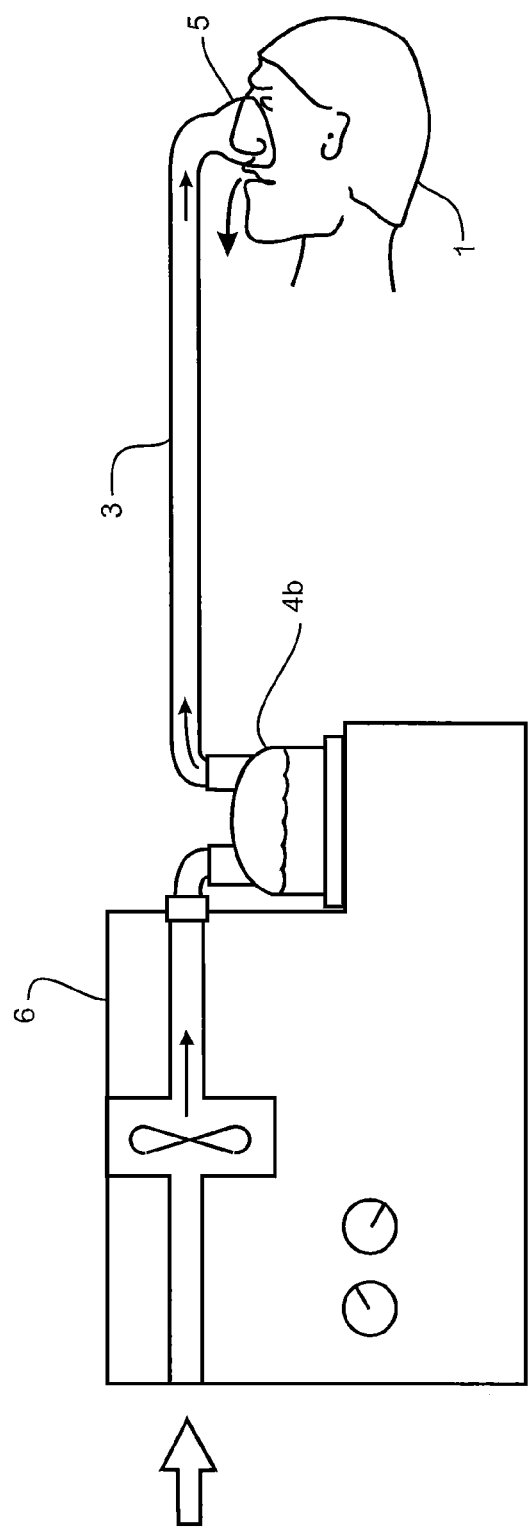
FIG. 2 is a schematic view of another known form of respiratory assistance apparatus in which the blower unit and humidifier unit are integrated into a single main housing.

The invention relates primarily to a flow path fault detection method and system for a respiratory assistance apparatus. By way of example, an embodiment of the flow path fault detection method and system will be described with reference to a respiratory assistance apparatus of the integrated system type in which the blower unit is integrated with the humidification unit in a single housing. However, it will be appreciated that the algorithm may be used in any other type of configuration, such as a modular type respiratory assistance apparatus in which the humidification unit is separate from the blower unit.

Further, the embodiment to be described is with reference to a respiratory assistance apparatus being used particularly for high-flow humidification therapy for the treatment of respiratory disorders such as COPD. The stream of gases may be atmospheric air or a mixture of atmospheric air augmented with a supplementary gas, such as oxygen or any other gases composition.

Embodiments of the flow path fault detection method may be configured to detect or sense a breakage, leak, and/or blockage along the gases stream flow path, and generate an indicative fault or warning signal to the control system and/or use to remedy the fault. Various examples of the fault detection method will be described.

In a first example that follows, the fault detection method is configured to detect a disconnected or removed component from the flow path, such as the removal of the humidification chamber from the flow path. If removal is detected, the fault detection method triggers an indicative warning that the humidification chamber has been removed from the humidification compartment or unit, or otherwise disconnected from the flow path. It will be appreciated that the fault detection method could additionally or alternatively be modified to detect the connection status (ie presence or absence) of other components in the flow path, such as the user interface (e.g. nasal cannula) of the patient interface, flexible conduit of the patient interface, and any inlet filter provided on the gases inlet of the respiratory assistance apparatus. The fault detection method may also be modified to identify or sense the type of components connected in the flow path, from a set of predetermined types. For example, the fault detection method could be modified to determine the type of nasal cannula installed, such as adult cannula (large, medium, small) or junior/paediatric cannula.

In a second example that follows, the fault detection method is configured to detect any leaks in the gases stream flow path extending from the outlet of the blower unit to the user interface at the patient. The leaks may vary in magnitude from small to large, and may be caused by removal of components from the flow path, such as the chamber or the user interface, faulty connections between components in the flow path, perforations or holes in the flexible conduit, or any other circumstance which may cause an unacceptable leak.

In a third example that follows, the fault detection method is configured to detect blockages in the gases flow path extending from the outlet of the blower unit to the user interface at the patient.

In a fourth example that follows, the fault detection method is configured to detect both leaks and blockages in the gases flow path extending from the outlet of the blower unit to the user interface at the patient.

Respiratory Assistance Apparatus

The various examples of the fault detection method will be described with reference to their operation in the context of the respiratory assistance apparatus 12 of FIG. 3. The respiratory assistance apparatus 12 comprises a blower unit (not visible) that generates a stream of pressurised or high-flow gases which are then heated and humidified by a humidification unit in a manner described previously in the background. The blower unit is situated within the main housing of the respiratory apparatus 12 and receives a supply of gases from a gases inlet located in the rear of the housing (not visible). The outlet of the blower unit is fluidly coupled by conduits or connectors to the humidification unit.

The humidification unit comprises a humidification chamber 14 that contains a volume of water. The humidification chamber 14 may be formed from a plastic or other suitable material that may have a highly heat conductive base (for example an aluminium or metal base), that is in direct contact with a heater plate 16 situated beneath the humidification chamber, and which is configured to heat the water within the humidification chamber. In this embodiment, the humidification chamber has an inlet or inlet port 18 that is fluidly connected or coupled to the outlet of the blower unit. The humidification chamber also comprises an outlet or outlet port 20 that is fluidly connected or coupled to the gases outlet 22 of the respiratory apparatus 12.

As will be appreciated, the high flow gases stream generated at the gases outlet 22 is delivered to a user 24 by a patient interface. In the embodiment shown, the patient interface comprises a flexible conduit or tube 26 that is connected at one end to the gases outlet 22 of the respiratory apparatus 12 and at the other end to a user interface in the form of a nasal cannula 28. As will be appreciated, the user conduit 26 may be heated by an integrated heating wire or element 30. While the user interface shown is a nasal cannula 28, any other suitable user interface could be used, including, but not limited to, a mask that covers the mouth and nose, a nasal mask covering the nose, a full face mask, a mouth-only interface or oral mask, or the end of the conduit can be connected to a tracheotomy fitting, or an endotracheal intubation.

The flow path of the gases stream in the respiratory system, comprising the respiratory apparatus 12 and patient interface 26, 28, can be considered as starting at the gases inlet of the respiratory apparatus 12 and flowing through the components of the system, including the blower unit, humidification chamber 14 of the humidification unit, user conduit 26, and terminating at the outlet(s) of the user interface 28.

The respiratory apparatus 12 comprises an electronic main controller or control system, which is configured to control the system, including the blower unit, humidification unit, and any user interface heating element in response to user settings which are input via an operable user input interface indicated at 30, which may comprise buttons, dials, touch screen input or any other type of electronic user interface. For example, the user may control the flow rate, temperature and humidity of the gases stream delivered to the user 24 via input settings at the user input interface 30.

The blower unit or flow generator comprises a motor-driven rotatable impeller or fan that is configured to draw in gases from the gases inlet and generate a pressurised gases stream or flow of gases in the flow path. The motor of the blower unit is a variable speed motor that is controlled by the control system or a motor speed controller via a motor speed control signal or signals to generate the desired flow rate of gases to the user.

Various sensors may be provided along the flow path for sensing various characteristics or parameters of the gases stream, including, but not limited to, temperature sensor(s), humidity level sensor(s), and flow rate sensor(s). The control system receives the signals indicative of the sensed characteristics by the sensors and operates the various components accordingly to deliver the desired type of gases stream to the end user. In this embodiment, the respiratory apparatus 12 at least comprises a flow rate sensor. In this embodiment, the flow rate sensor is located in the flow path between the gases inlet and the blower unit and generates a flow rate signal indicative of the sensed or measured flow rate, and the flow rate signal is sent to the control system. The control system may use the flow rate signal for closed-loop feedback control of the blower unit motor speed to deliver a user set flow rate. For example, the motor speed is varied to minimise the error or difference between the sensed flow rate and user set flow rate, as will be appreciated.

The flow rate sensor may, for example, be in the form of a hot-wire anemometer (HWA) flow detector, but any other suitable flow rate sensor or flow probe could be used. The flow rate sensor need not be located in the flow path prior to the blower unit but could be located anywhere in the flow path prior to the humidification chamber.

The control system comprises a programmable controller, such as a microprocessor, microcontroller or digital signal processor, and has associated memory. The programmable controller may execute software commands stored in the associated memory. As mentioned, the control system receives input from sources such as the user input interface 30 and any sensors, and controls the system components such as the motor speed of the blower unit, energy level of the heater plate 16 in the humidification unit, and conduit heater wire 30 to deliver the flow of gases at the desired humidity and/or temperature and/or flow rate set by the user.

First Example—Flow Path Fault Detection Algorithm—Humidification Chamber Connection Status In this first example, the fault detection method is configured to detect if the humidification chamber is removed or disconnected, either completely or partially, from the flow path.

The flow rate delivered by the respiratory apparatus is primarily determined by the motor speed of the blower unit and the air flow resistance in the flow path downstream of the blower unit. If there are significant leaks, breakages or disconnected components in the gases flow path, this will alter the air flow resistance in the flow path and therefore the flow rate generated for a particular motor speed. Such faults in the expected flow path may alter the correct operation of the control system and its ability to deliver the desired flow rate to the user. Therefore it is desirable for the control system to automatically detect such faults and warn the user.

In this example, the humidification chamber 14 is removable from the humidification unit for cleaning and/or refilling or replacement, as will be appreciated. The humidification chamber represents a significant air flow resistance component in the flow path after the blower unit. Removal or dislodgement of the humidification chamber from the respiratory apparatus 12 causes a higher flow rate to be generated by the blower unit for a given motor speed, than if the humidification chamber was installed (connected in the flow path in normal operation).

In this example, the control system implementing the fault detection method is configured to automatically determine whether the humidification chamber is removed or disconnected, either entirely or partially, from the flow path and then responds accordingly by, for example, triggering a user alarm (audible and/or visual) and/or halting operation of the unit or shutting down the unit or placing it in standby mode.

Figure 4:
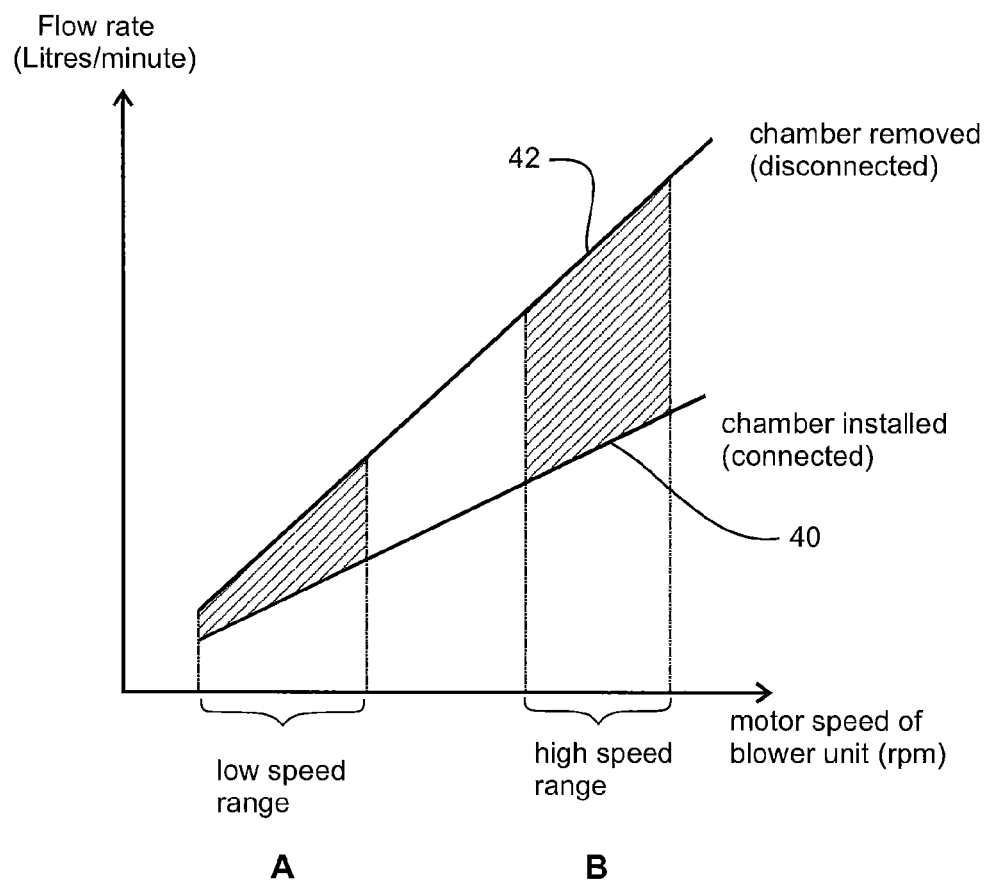
FIG. 4 is a graphical representation of the flow rate versus motor speed characteristic for the respiratory assistance apparatus of FIG. 3 showing the differences in the flow rate when the humidification chamber is installed (connected) and removed (disconnected) over a motor speed range for the blower unit.

Referring to FIG. 4, it has been discovered that the detection of the chamber connection status (i.e. removed/disconnected or installed/connected) is easier to determine at a higher motor speed range than a lower motor speed range. FIG. 4 shows schematically a typical flow rate versus motor speed characteristic line 40 for when a chamber is installed and a characteristic line 42 representing the flow rate versus motor speed when the chamber is removed. Based on flow rate sensed in the flow path between the blower unit and the humidification chamber. As shown, the difference between the lines 40,42 increases with speed. Therefore, it is easier to determine definitively (or with a lower false alarm rate) based on a sensed flow rate reading at a higher motor speed range as to whether the chamber is removed or installed, e.g. in region B, than at a lower speed range, e.g. in region A where the difference between the flow rates is smaller and therefore carries a higher probability of false alarms.

Fault Detection Algorithm Steps—First Embodiment—Flow Rate Sensing at Two Controlled Motor Speeds In a first embodiment, the flow path fault detection method is configured to detect the humidification chamber connection status (i.e. installed/connected or removed/disconnected) based on the sensed flow rate and motor speed of the blower unit using a two-stage sensing approach of flow rate at two different motor speeds. The fault detection algorithm may be executed by the control system either continuously, or periodically at preset time intervals or during particular system operations or in particular modes, e.g. upon start up, or at any other suitable time. When running the fault detection algorithm, the control system receives a sensed flow rate signal from the flow rate sensor located between the blower unit and the humidification chamber and a motor speed signal indicative of the motor speed of the blower unit is either received from a motor speed sensor or otherwise derived by the control system.

Figure 5:
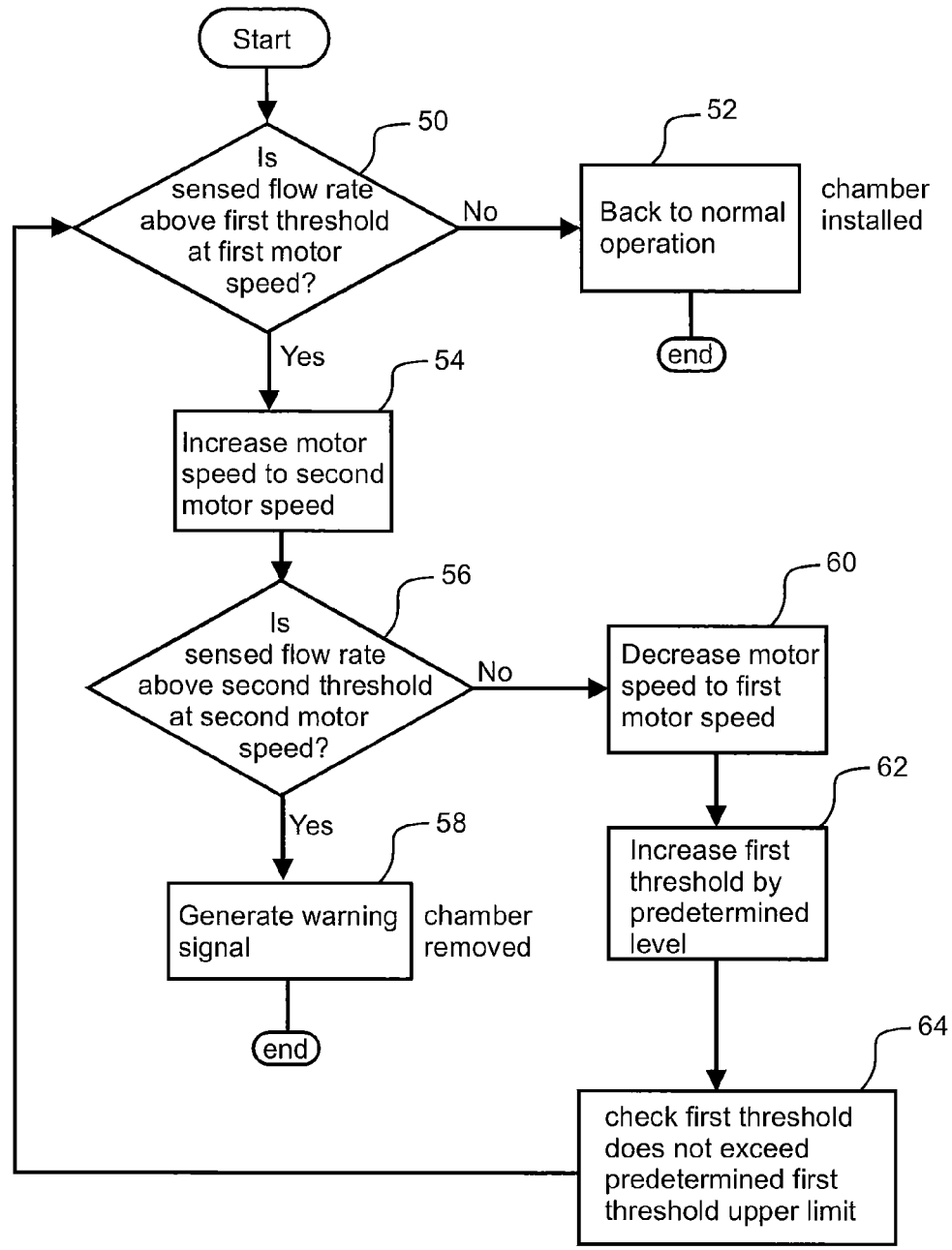
FIG. 5 is a flow diagram depicting the main steps of a first example of the flow path fault detection algorithm configured to determine if the humidification chamber has been removed or disconnected from the flow path in accordance with a first embodiment of the invention.

Referring to FIG. 5, the typical steps in the fault detection method will be described. During operation, the fault detection method starts with step 50 which comprises determining if the sensed flow rate is above a first threshold at a first motor speed. In this first embodiment, the fault detection algorithm is run continuously or periodically by the control system in that step 50 is initiated or performed periodically at a predetermined sample rate of the flow rate sensor signal or for every new sensed flow rate sample.

As mentioned, the sensed flow rate is based on the flow rate signal generated by the flow rate sensor. The first threshold is a predetermined flow rate threshold that is stored in memory for the first motor speed. The first motor speed may be the current operating motor speed of the device in normal operation. Alternatively, the fault detection algorithm may increase or decrease the current motor speed to a predetermined stored first motor speed within a predetermined first motor speed range 106 upon initiation of the algorithm.

If the first threshold is not exceeded, the algorithm reverts to normal operation at step 52 and ends, ready for initiating at step 50 again for the next sensed flow rate sample. If the first threshold is exceeded, the fault detection algorithm then increases the motor speed of the blower unit to a second motor speed as shown at step 54. The second motor speed may be within a predetermined stored second motor speed range that is above the first motor speed range 106. In one form, the decision to move to step 54 may be based on a single flow rate sample that exceeds the first threshold. In an alternative form, the decision to move to step 54 may require a predetermined number of multiple successive flow rate samples to exceed the first threshold, to reduce the likelihood of a false alarm triggering.

Once operating at the second motor speed, the fault detection algorithm then determines whether the sensed flow rate is above a second threshold representing a predetermined stored flow rate threshold for the second motor speed.

If the second threshold is exceeded (as determined based on a single flow rate sample or multiple successive flow rate samples as above), then the algorithm generates a warning signal or fault detection signal 58 indicating that the humidification chamber is disconnected or removed and then the algorithm ends. The control system may respond to the warning signal by triggering an audible or visual alarm or modifying operation of the respiratory apparatus, for example shutting down the blower unit or otherwise entering a standby mode.

If the second threshold is not exceeded (as determined based on a single flow rate sample or multiple successive flow rate samples as above), then the motor speed is decreased back to the first motor speed at 60. The first threshold is then increased or incremented by a predetermined level or quantity at 62. At step 64, the modified first threshold is then compared with a first threshold upper limit. The modified first threshold must not exceed a predetermined stored upper limit level and if it does the modified first threshold is fixed at the upper limit threshold. The modified first threshold is stored and then used for future loops of the algorithm, unless it is modified again by a subsequent or future loop of the algorithm. In some embodiments, any modifications to the first threshold are reset after any warning signal is generated by a subsequent loop. This means the algorithm is reset to its initial values ready for operation again once the fault has been remedied.

At the conclusion of step 64, the fault detection method loops back to step 50 and checks the sensed flow rate against the modified first threshold and repeats the steps above one or more times, until terminating at one of the exit points or ends.

Flow Rate Thresholds

Figure 6:
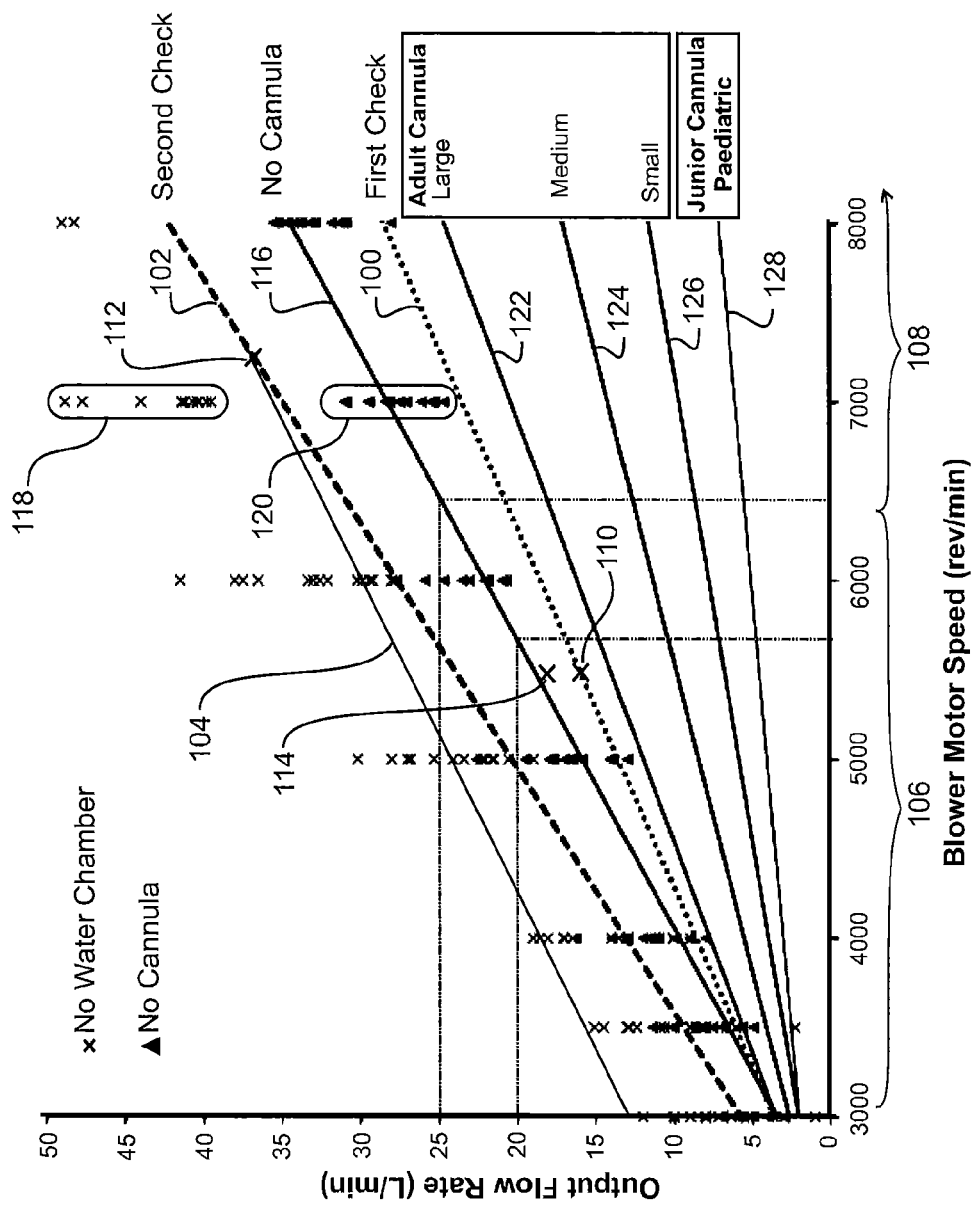
FIG. 6 shows a graphical representation of the stored threshold lines that are used in the flow path fault detection algorithm of FIG. 5 and flow rate versus motor speed characteristic lines for various flow path configurations based on experimental results.

Referring to FIG. 6, the flow rate thresholds stored and used by the fault detection method will be explained in further detail. The thresholds may be discrete thresholds at predetermined motor speeds, or alternatively threshold lines or curves defining multiple or continuous flow rate thresholds over a range of motor speeds may be stored. Such threshold lines may be in the form of straight lines representing flow rate threshold versus motor speed characteristics having an offset and gradient as shown in FIG. 6. Alternatively, the threshold lines may be any other curved or arbitrary profile defined by formula or plotted between discrete points.

Figure 3:
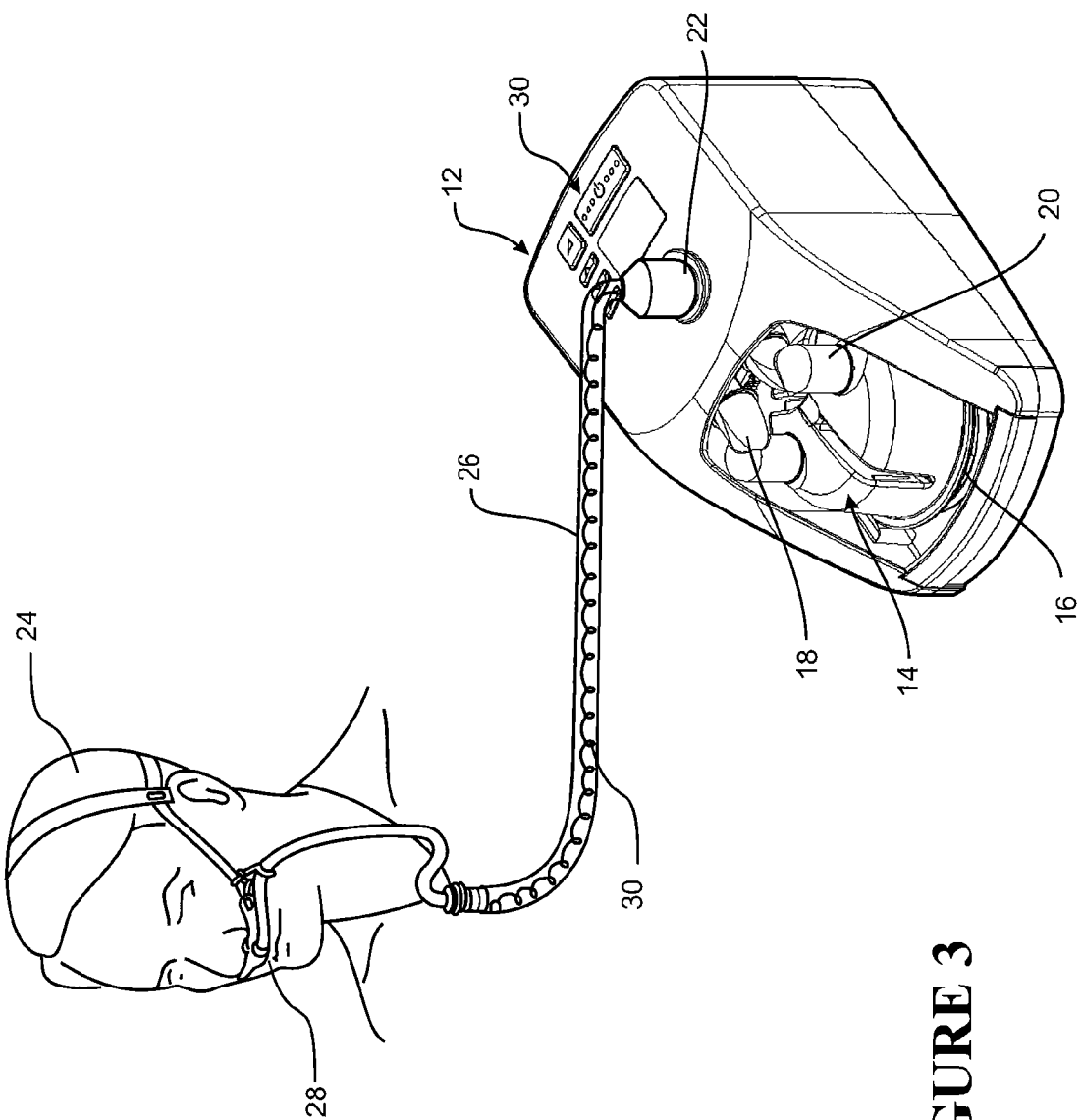
FIG. 3 is a perspective view of a respiratory assistance apparatus in accordance with an embodiment of the invention delivering a flow of gases to a user via a nasal cannula.

FIG. 6 shows an average flow rate versus motor speed characteristic line 116 for when the humidification chamber is connected in the flow path, but where there is no cannula 116 connected to the end of the flexible conduit 26 of the patient interface, generated by experimental operation of a respiratory assistance apparatus of the type shown in FIG. 3. At various motor speeds (e.g. 3000 rpm, 3500 rpm, 4000 rpm, 5000 rpm, 6000 rpm, 7000 rpm, 8000 rpm) along this line 116, the flow rate was sampled for when the gases flow path comprises a connected humidification chamber and no cannula. By way of example, the set of flow rate samples for a motor speed of 7000 rpm is shown at 120. The other flow rate samples at the other speeds are represented by the sample graph symbols. Likewise, the flow rate was sampled for the same gases flow path, but with the humidification chamber removed/disconnected and these samples are plotted on the graph by the symbols indicated at 118. As shown, the flow rate samples 118,120 overlap considerably at the lower speeds, making it difficult to determine a flow rate that indicates the chamber has been disconnected, as was explained with reference to FIG. 4. However, as the speed increases, the overlap between the sets of samples 118,120 reduces and they become sufficiently distinct from one another such that it is easier to determine a flow rate that represents when the chamber has been removed.

FIG. 6 also shows the flow rate versus motor speed characteristic for a gases flow path comprising a number of different types of connected cannula, such as a large adult cannula 122, a medium adult cannula 124, a small adult cannula 126, and a junior cannula 128 for paediatric users. It will be appreciated that the flow rate could be compared against thresholds based on these characteristic lines to assist in identifying or determining the type of cannula connected in the gases flow path, in a modified form of the fault detection algorithm.

In this embodiment, the first threshold line 100 is situated below the second threshold line 102. The purpose of this is that the first threshold line represents a conservative (high sensitivity) threshold in the first-stage of sensing for detecting whether the sensed flow rate is indicative of chamber disconnection or removal for motor speeds in the a first speed range 106. The first speed range typically covers the range of motor speeds where there is some overlap between the flow rate samples 118,120. For the experimental respiratory assistance apparatus used for generating FIG. 6, there is no overlap and sufficient displacement between the flow rate samples at approximately 6500 rpm, or when the flow rate is about 25 L/min. In this embodiment, the first speed range for sensing the flow rate against the first threshold is therefore defined at any motor speed in the motor speed range required to generate a flow rate below approximately 25 L/min in the gases flow path, which for the experimental apparatus for a gases flow path with no cannula is a motor speed below 6500 rpm. The second speed range for sensing the flow rate is defined as any motor speed in the motor speed range required to generate a flow rate at or above 25 L/min in the gases flow path, which for the experimental apparatus for a gases flow path with no cannula is a motor speed at or above approximately 6500 rpm.

In one preferred embodiment, the first speed range is the motor speed range required to generate a flow rate of at or below approximately 20 L/min (motor speeds at or below approximately 5700 rpm in the experimental apparatus for a gases flow path with chamber but no cannula) and the second speed range is the motor speed range required to generate a flow rate at or above 25 L/min (motor speeds at or above approximately 6500 rpm in the experimental apparatus for a gases flow path with chamber but no cannula). The first and second speed ranges are defined relative to flow rate generated rather than absolute speed values because the respiratory apparatus may comprise motors having different power and speed characteristics, and because the gases flow path may or may not comprise a connected cannula, and any connected cannula may have a varied size and therefore air flow resistance component.

The first threshold line 100 is conservative in that the flow rate threshold versus motor speed profile characteristic may be generated based on the characteristic profile of the flow rate versus motor speed should the flow path air resistance be reduced by a level smaller than that of removing the humidification chamber. For example, the first threshold line may be set based on the expected flow rate versus motor speed characteristic for a flow path in which the nasal cannula or user conduit has been removed from the flow path. In this embodiment, the first threshold line 100 is a line extending below the flow rate versus motor speed characteristic line 116 for the gases flow path comprising the chamber but no cannula. In this embodiment, the first threshold line extends between line 116 and line 122 representing the flow rate versus motor speed characteristic for a gases flow path comprising the chamber and a large adult cannula connected. The first threshold therefore does not definitively indicate that the humidification chamber has been disconnected or removed from the gases flow path, but signals that there may be some modification (reduction) to the gases flow path resistance and therefore some possible fault. The first threshold has an associated probability of false alarm that is higher than that associated with the second threshold.

The second threshold line 102 is based on the true or expected flow rate versus motor speed characteristic with the humidification chamber removed from the gases flow path. The second threshold line 102 represents the second threshold at the second higher motor speed range 108 which the sensed flow rate is compared to in the second-stage of sensing in the fault detection method. As shown, the second threshold line is above or exceeds the first threshold line along the motor speed range axis.

An example of the operation of the fault detection algorithm with numerical values will now be described, although it will be appreciated that these values may be altered and are included as an exemplar only. As shown in FIG. 6, the fault detection method may operate with a first motor speed of 5500 rpm, which corresponds to a first flow rate threshold of approximate 15 L/min as indicated at 110. If the sensed flow rate at 5500 rpm does not exceed 15 L/min, then no warning signal is generated and the respiratory apparatus operates as normal. If the sensed flow rate exceeds 15 L/min, then the motor speed of the blower unit is increased or ramped to a second higher motor speed such as approximately 7100 rpm, in which case the second flow rate threshold applies corresponding to approximately 36 L/min as indicated at 112. If the sensed flow rate at 7100 rpm exceeds 36 L/min, then a warning signal is generated indicating the humidification chamber has been removed or is disconnected from the flow path. Alternatively, if the 36 L/min second threshold is not exceeded, then the algorithm reduces the motor speed back to 5500 rpm and increases the first threshold 110 by a predetermined level, e.g., to say 16 L/min as indicated at 114, toward an upper limit line 104. The sensed flow rate is then compared against the modified first threshold 114 and repeats the algorithm from step 50 one or more times as previously indicated until terminating at one of the exit points.

The purpose of modifying the first threshold is to prevent the algorithm from oscillating back and forward between first and second threshold sensing stages in an endless loop. As mentioned, the first threshold will not be increased beyond the predetermined upper limit line 104. If only a single discrete first motor speed is employed by the fault detection method, then the first threshold at that motor speed need only be modified (increased). However, if the fault detection method assesses the sensed flow rate against any arbitrary motor speed in the first motor speed range (thereby requiring a first threshold line representing the flow rate threshold over a range of motor speeds), the modification of first threshold may require modification of the entire first threshold line, e.g., increasing the gradient and/or offset.

Purpose of Two-Stage Sensing

The fault detection method above is based on comparing the sensed flow rate against two different thresholds, at two different motor speeds. The purpose of the dual speed or two-stage sensing approach of fault detection is to reduce or minimize the chances of false alarms, e.g., a warning signal being generated incorrectly when the chamber is installed correctly. The first motor speed is typically in a first motor speed range that is in the normal operating speed range for generating typical flow rates for high flow therapy. However, at such speed ranges, the difference between the sensed flow rate when the chamber is installed and removed is small, and it is difficult to discriminate between the two, making the threshold level difficult to set without either creating a high probability of false alarms (sensitivity too high), or alternatively, not adequately detecting legitimate faults (sensitivity too low). The two-stage or multi-stage sensing approach addresses this issue.

As explained above, the first threshold in the first speed range is set at a conservative level having an associated higher probability of false alarms for indicating chamber disconnection/removal relative to the second threshold. However, such false alarms are filtered out by the second threshold detection stage, in which the motor speed is increased to the second higher motor speed range where the difference between the flow rate versus motor speed characteristic between when the chamber is installed and when it is removed, is more prominent (easier to discriminate as shown and explained previously with reference to FIG. 4), and the sensed flow rate is then compared to a second threshold at this higher, second motor speed. The second threshold is set to a value having a lower probability of false alarms compared with the first threshold at the lower first speed range. As explained above, the fault detection method described herein also alters the first threshold dynamically such that it calibrates the first threshold for the particular respiratory apparatus configuration, and thus, increases detection efficacy. In particular, the first threshold line is progressively modified or fine tuned during operation of the algorithm to a value having a reduced probability of false alarms relative to its original value.

Implementation

The methods or algorithms as described above may be implemented in hardware, software, firmware, middleware, microcode, or any combination of these. By way of example, the methods or algorithms may be embodied directly in hardware, in a software module executable by a processor, or a combination of these, and may be in the form of a processing unit or programmable instructions, and may be contained in a single device or distributed across multiple devices. The software module may reside in any form of memory, including RAM memory, flash memory, ROM memory, EPROM memory, EEPROM memory, registers, hard disc, removable disc, CD-ROM or any other form of storage medium. A storage medium or memory may be coupled to the processor such that the processor can read information from, and write information to, the storage medium. In an alternative embodiment/form, the storage medium may be integral to the processor. The methods may also be provided in a computer-readable medium having stored thereon computer executable instructions that, when executed on a processing device, cause the processing device to perform the method or methods.

Figure 7:
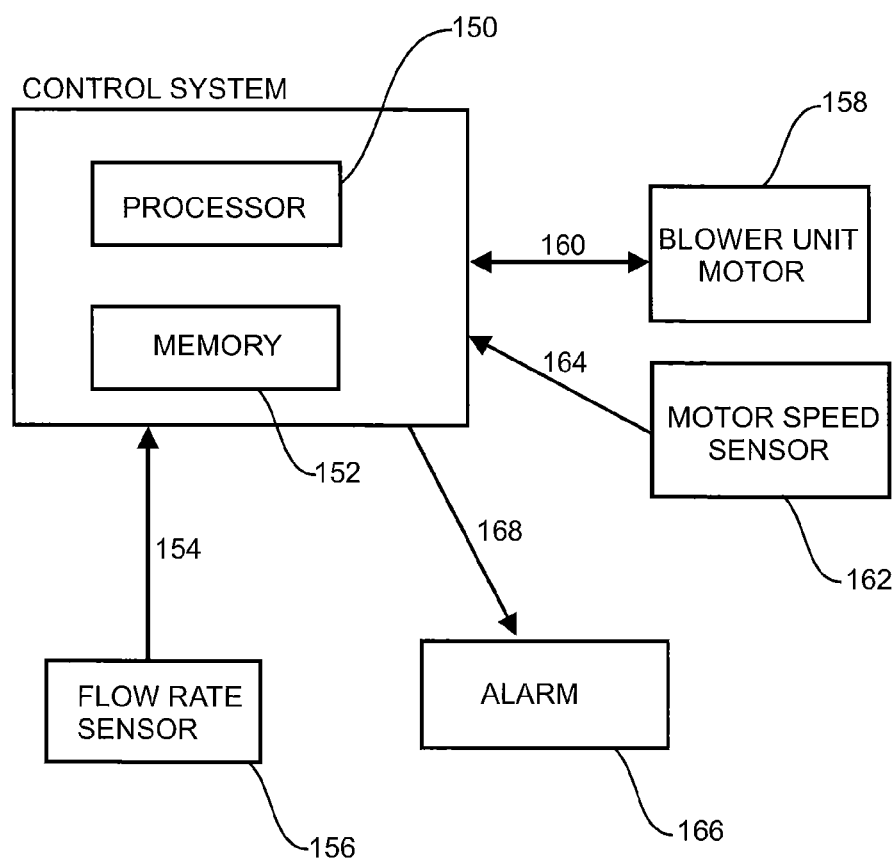
FIG. 7 shows a schematic representation of the main hardware components carrying out the flow path fault detection algorithm in accordance with an embodiment of the invention.

Referring to FIG. 7, an example of one possible hardware configuration for implementation of the fault detection method will be described. As mentioned, the control system of the respiratory assistance apparatus 12 typically at least comprises a programmable processor 150 and associated memory 152. In the context of the fault detection method, the method or algorithm is implemented in software defined by programmable instructions that are stored in memory 152 and implemented by the processor 150 to carry out the algorithm steps described above with reference to FIG. 5. The various flow rate thresholds and motor speeds are stored in memory and retrieved by the processor during operation.

As shown, the control system receives a flow rate signal 154 from the flow rate sensor 156 that is situated in the flow path between the blower unit and humidification chamber and which generates the flow rate signal which is indicative of the flow rate in the flow path. The control system also communicates with the motor 158 of the blower unit. In particular, the control system sends control signals to the blower unit motor to control the motor speed during operation of the respiratory apparatus, and a motor speed sensor 162 may also be provided which generates a motor speed signal 164 indicative of the motor speed. An alarm 166, which may be audible and/or visual, e.g., displayed on the user input interface, may be provided for alerting the user to a fault detection, e.g., when the chamber is removed or disconnected during use. The control signal system may trigger the alarm 166 by an alarm control signal 168.

Figure 8:
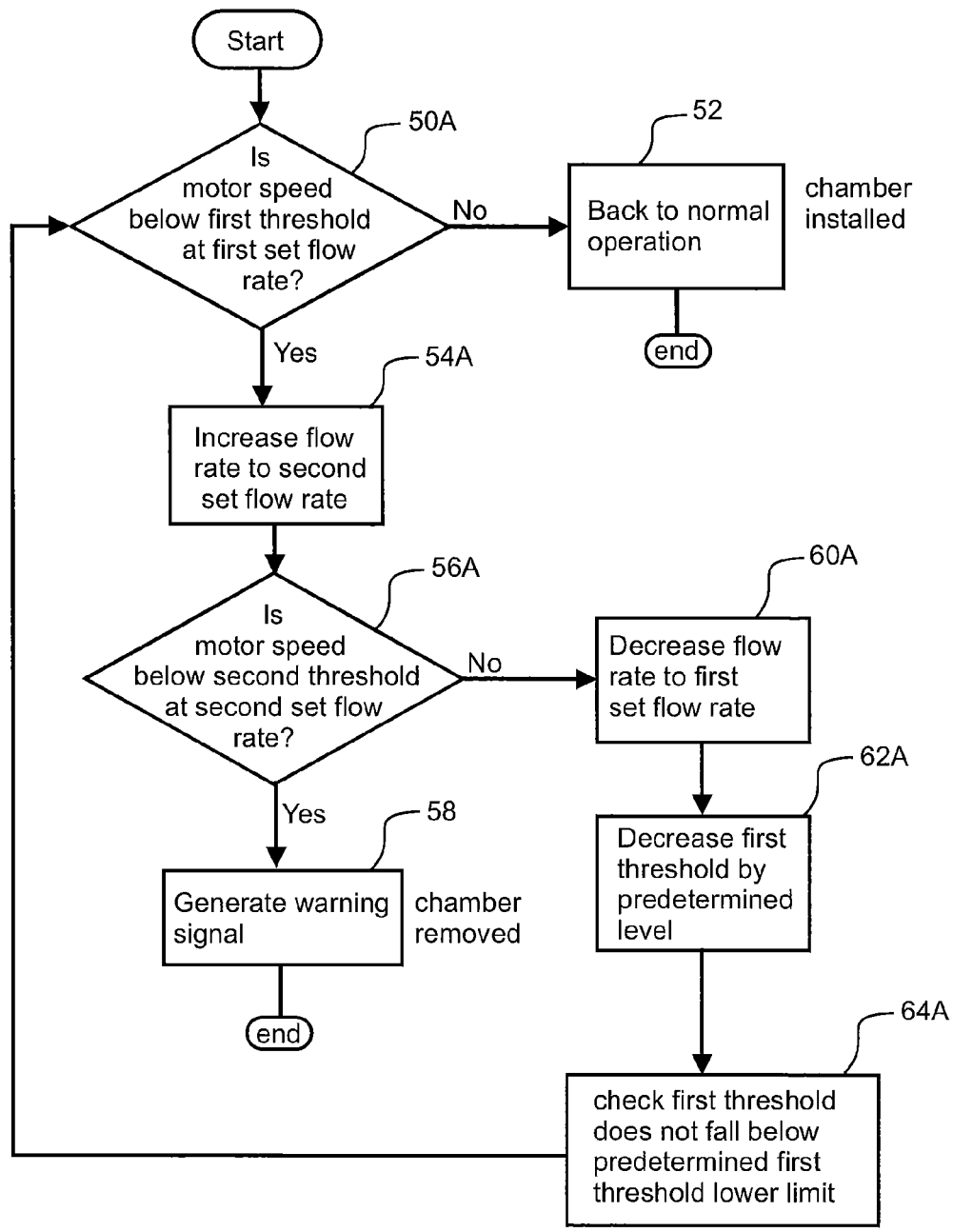
FIG. 8 is a flow diagram depicting the main steps of a variant of the first example of the flow path fault detection algorithm configured to determine if the humidification chamber has been removed or disconnected from the flow path in accordance with a second embodiment of the invention.

Fault Detection Algorithm Steps—Second Embodiment—Motor Speed Sensing at Two Controlled Flow Rates As will be appreciated, the flow rate of the gases in the gases flow path is largely proportional to the motor speed for a given respiratory assistance apparatus configuration. In the first embodiment, the fault detection algorithm controls the motor speed and at each of the two stages of sensing compares the flow rate sensed to flow rate thresholds at two different motor speeds based on the principle that an increased generated flow rate at any particular motor speed represents a loss in air flow resistance in the gases flow path. However, it will be appreciated that the fault detection algorithm may be modified such that it controls the flow rate generated, and at each of the two stages of sensing, compares the motor speed required to generate the set flow rate against motor speed thresholds at each different flow rate, based on the principle that a reduced motor speed required to generate a set flow rate, represents a loss in the gases flow path resistance. FIG. 8 shows a second embodiment of the fault detection method which is implemented in this way.

Referring to FIG. 8, the operation of the second embodiment fault detection method is similar to the first, except that the set flow rate is controlled and the motor speed is sensed or determined and compared against thresholds. The primary differences will be explained below, but all other aspects are substantially the same.

Starting at step 50A, the sensed motor speed is compared against a first motor speed threshold at a first set flow rate. The first set flow rate may be the current operating flow rate or the control system may control the motor speed to generate the first set flow rate. If the motor speed is above the first threshold, then the algorithm exits at 52. If the motor speed is below the first threshold, then the flow rate is increased to a higher second set flow rate at 54A.

At step 56A, the sensed motor speed required to generate the higher second set flow rate is then compared against a second threshold motor speed. If the sensed motor speed falls below the second threshold motor speed, then a warning signal is generated at 58 indicating that the chamber has been removed or disconnected or at least partially dislodged from the gases flow path.

If the sensed motor speed exceeds the second threshold motor speed, then the set flow rate is reduced to the first set flow rate at 60A, and the first motor speed threshold is reduced by a predetermined level. The first threshold is not allowed to go below a first threshold lower limit, and is fixed at that lower limit if it does. The algorithm then loops back to the start step 50A and recompares the motor speed with the modified first threshold and repeats the algorithm steps until exiting.

In this second embodiment (like the first), the first set flow rate is in the range of below 25 L/min, and the second set flow rate is in the range of at or above 25 L/min. In one preferred embodiment, the first set flow rate is at or below 20 L/min, and the second set flow rate is at or above 25 L/min.

Fault Detection Algorithm Steps—Other Embodiments—Mixture of First and Second Embodiments In other embodiments, it will be appreciated that a mixture of the sensing stages of FIGS. 5 and 8 may be used. For example, in one embodiment, steps 50, 60, 62, and 64 in FIG. 5 may be replaced by steps 50A, 60A, 62A, and 64A of FIG. 8 respectively. In another embodiment, steps 50A, 60A, 62A, 64A in FIG. 8 may be replaced with steps 50, 60, 62, and 64 of FIG. 5 respectively.

Second Example—Flow Path Fault Detection Algorithm—Leak Detection

The fault detection algorithm in the first example was configured to detect the disconnection, removal or dislodgement, whether partial or complete, of the humidification chamber from the gases flow path and to generate an indicative warning signal for the control system to take a fault action, such as halt the system operation and/or trigger an alarm to the user or similar. This sort of disruption to the gases flow path or breathing circuit can be considered as one type of leak. However, other leaks in the gases flow path may also be caused by other circumstances, including, but not limited to, removal of the user interface such as the cannula from the conduit, a faulty or unsealed connection between the conduit and outlet of the housing in the respiratory apparatus, a faulty or unsealed connection between the cannula and the end of the conduit, a hole or perforation in the wall of the conduit, or any other circumstances causing a leak in the gases flow path. It will be appreciated that the thresholds in the fault detection method described in the first example can be modified to be more sensitive such that they detect any unacceptable leak ranging in magnitude from complete removal of the chamber as in the first example to a more minor leak caused by a faulty connection or perforation in the conduit. The flow charts described with reference to FIGS. 5 and 8 and the other variants described are equally applicable for a fault detection method configured to detect all such leaks.

The fault detection method for leaks may be configured to operate in different modes, suitable to different flow path configurations. For example, the fault detection system method may operate in a first mode for a first type of cannula (e.g. adult mode for an adult cannula), and a second mode for a second type of cannula (e.g. junior mode for a pediatric cannula). In each of the different modes, the thresholds and associated motor speed ranges and/or set flow rate ranges may be varied to suit the specific flow path configuration characteristics such as the expected normal air flow path resistance of the different configurations.

In one example configuration of the apparatus of FIG. 3, the apparatus is operating in adult mode with an adult cannula at the end of the conduit. In this adult mode configuration, after detecting (e.g. step 50 in FIG. 5) the sensed flow rate is above the first threshold at the first motor speed (e.g. normal operating speed), the fault detection method is configured to ramp the motor to a second motor speed (e.g. step 54 in FIG. 5) that is at least (i.e. equal to or above) 6000 rpm for re-sensing the flow rate against the second threshold (e.g. step 56 in FIG. 5). However, when the apparatus is operating in junior mode with a pediatric cannula at the end of the conduit, the fault detection method is configured to ramp to a second motor speed that is at least 4000 rpm for re-sensing of the flow rate against the second threshold.

Third Example—Flow Path Fault Detection Algorithm—Blockage Detection

In addition to detecting leaks in the gases flow path as described in the previous examples, the fault detection method may be configured to detect blockages in the gases flow path as will be explained in this third example with reference to FIG. 9. Like with the leak detection, it has been discovered that it is generally more difficult to distinguish between acceptable flow rate values and overly low flow values, which could indicate a blockage, when the respiratory assistance apparatus is set to operate at low motor speeds or flow rates. It has been discovered that it is easier to distinguish between normal or acceptable flow rates and flow rates that are indicative of a blockage in the gases flow path at higher motor speeds and/or flow rates.

Figure 9:
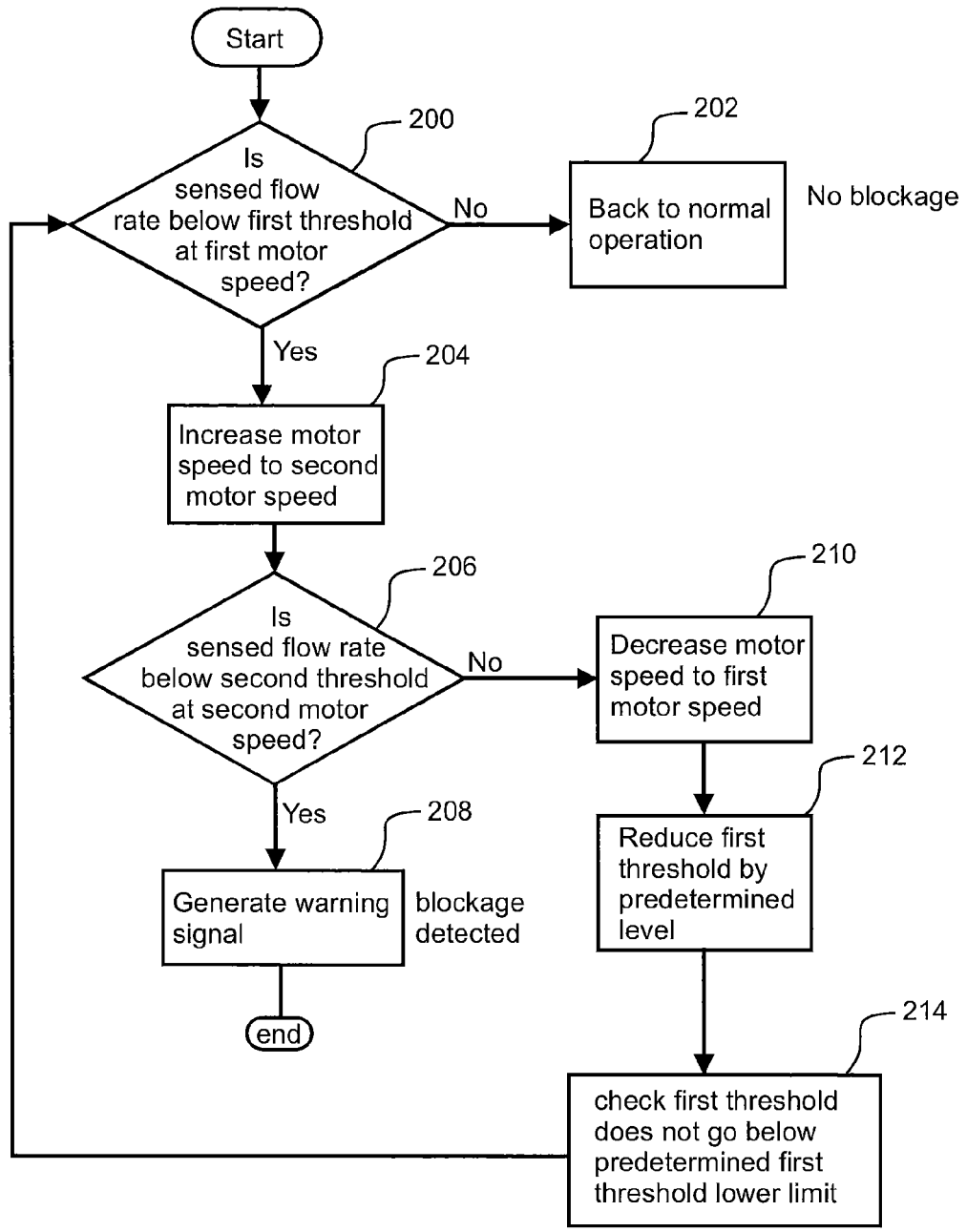
FIG. 9 is a flow diagram depicting the main steps of a third example of the flow path fault detection algorithm configured to determine if there is a blockage in the flow path in accordance with an embodiment of the invention.

Referring to FIG. 9, the fault detection method can be configured to detect blockages in a similar but modified approach to the previous examples. During operation, the fault detection method for blockages starts with step 200 which comprises determining if the sensed flow rate is below a first threshold at a first motor speed. The fault detection algorithm may be run continuously or periodically by the control system in that step 200 is initiated or performed periodically at a predetermined sample rate of the flow rate sensor signal or for every new sensed flow rate sample. The first threshold is a predetermined flow rate threshold that is stored in memory for the first motor speed. The first motor speed may be the current operating motor speed of the device in normal operation. As will be appreciated from the previous examples, the first threshold for that motor speed may be extracted or determined from a first threshold line that extends across a first motor speed range. If the sensed flow rate is above the first threshold, the algorithm reverts to normal operation at step 202 and ends, ready for initiating at step 200 again for the next sensed flow rate sample. This means that no blockage has been detected.

If the sensed flow rate is below the first threshold, the fault detection algorithm then increases the motor speed of the blower unit to a second higher motor speed as shown at step 204. The second motor speed may be within a predetermined stored second motor speed range that is above the first motor speed range. Once operating at the second higher motor speed, the fault detection algorithm determines whether the sensed flow rate is below a second threshold representing a predetermined stored flow rate threshold for the second motor speed as shown at step 206. If the sensed flow rate is below the second threshold, the algorithm generates a warning signal or fault detection signal as shown at 208 indicating that a blockage has been detected. The control system may then respond accordingly to the warning signal by triggering an audible or visual alarm or modifying operation of a respiratory apparatus, for example shutting down the blower unit or otherwise entering a standby mode.

If the sensed flow rate is above the second threshold, then the motor speed is decreased back to the first motor speed as shown at step 210. The first threshold is then decreased by a predetermined level or quantity as shown at step 212. The modified first threshold is then compared with a first threshold lower limit. The modified first threshold must not go below this predetermined stored lower limit level and if it does the modified first threshold is fixed at the lower limit threshold level as shown at 214. The modified first threshold is then stored and used for future loops of the algorithm, unless it is modified again by a subsequent or future loop of the algorithm. Any modifications to the first threshold can be reset after a warning signal is generated by a subsequent loop so that the algorithm is reset to its initial values ready for operation once the fault has been remedied.

At the conclusion of step 214, the fault detection method loops back to the start 200 and checks the sensed flow rate against the modified first threshold and repeats the steps above one or more times, until terminating at one of the exit points or ends.

Like with the leak detection, the first threshold is highly sensitive and is set to have a higher associated probability of false alarm relative to the second threshold, which is set based on the true or expected flow rate versus motor speed characteristic for a flow path having a blockage.

Like with the leak detection, the fault detection method for blockage detection may be configured with settings that suit different apparatus modes of operation and/or flow path configurations. In one example configuration of the apparatus of FIG. 3, the apparatus is operating in adult mode with an adult cannula at the end of the conduit. In this adult mode configuration, after detecting (e.g. step 200 in FIG. 9) the sensed flow rate is below the first threshold at the first motor speed (e.g. normal operating speed), the fault detection method is configured to ramp the motor to a second motor speed (e.g. step 204 in FIG. 9) that is at least (i.e. equal to or above) 2000 rpm for re-sensing the flow rate against the second threshold (e.g. step 206 of FIG. 9). However, when the apparatus is operating in junior mode with a pediatric cannula at the end of the conduit, the fault detection method is configured to ramp to a second motor speed that is at least 6600 rpm for re-sensing of the flow rate against the second threshold.

Fourth Example—Flow Path Fault Detection Algorithm—Combined Leak and Blockage Detection It will be appreciated that the fault detection methods for determining leaks and blockages as described in the previous examples may be combined into a single fault detection method that is configured to detect both leaks and blockages. By way of example, referring to FIG. 10, the system may operate the leak detection algorithm based on a first leak threshold 220 and a second leak threshold 222 (equivalent to the first and second thresholds described in the previous examples relating to leak detection), and the blockage detection algorithm based on a first blockage threshold 224 and a second blockage threshold 226 (equivalent to the first and second thresholds described in the previous example relating to blockage detection). As will be appreciated, the sensed flow rate is continuously or periodically compared against the first thresholds 220, 224 at a first lower motor speed range 228 (e.g. normal operating range) for possible leaks or blockages. If a possible leak or blockage is detected in the first motor speed range 228, the motor speed is ramped to a higher second motor speed range 230 where the sensed flow rate is compared against the relevant second threshold 222 or 226 depending on whether a possible leak or blockage was detected. As described in the previous examples, the first threshold represents a conservative (high sensitivity) threshold and the second thresholds are based on a true or expected flow rate versus motor speed characteristic for the gases flow path which would indicate either an unacceptable leak or blockage, respectively. In particular, the first thresholds have an associated probability of false alarm that is higher than that associated with the corresponding second thresholds. The leak thresholds are above the blockage thresholds as shown.

Figure 10:
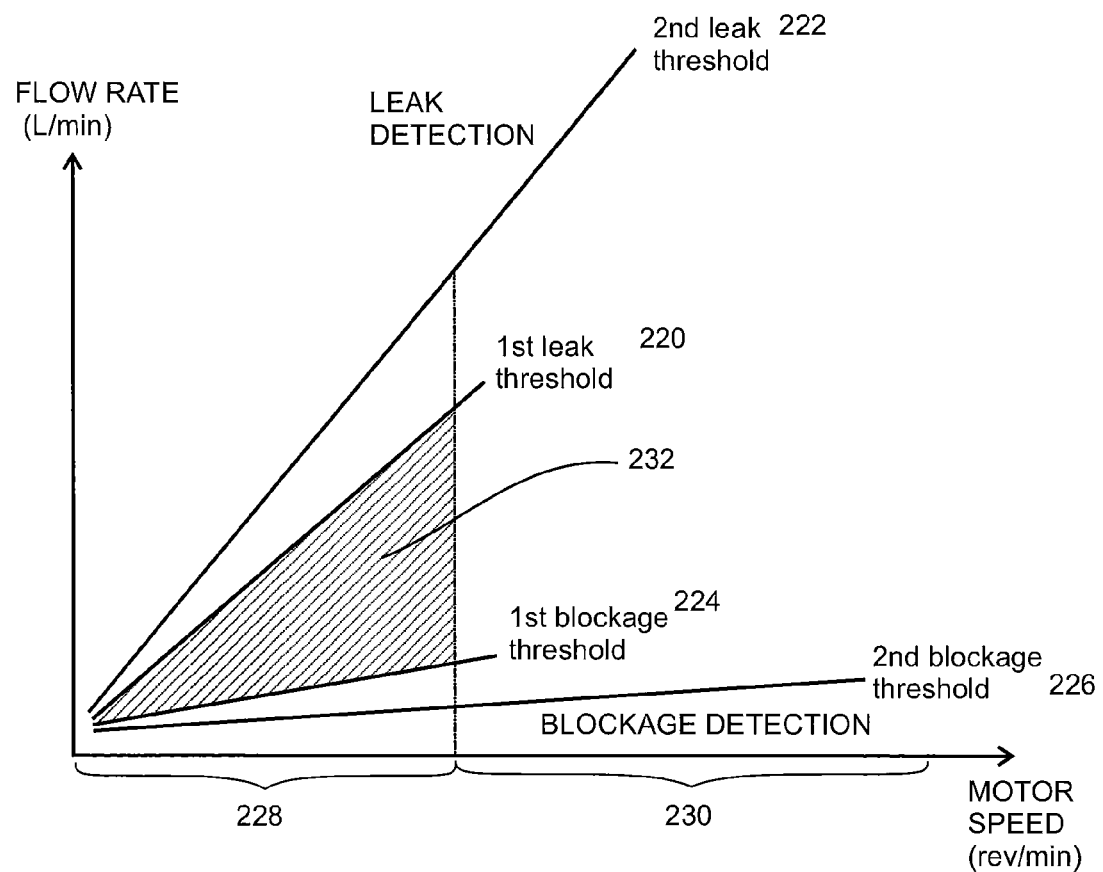
FIG. 10 shows a graphical representation of the stored threshold lines that are used in a fourth example of the flow path detection algorithm that is configured to detect both leaks and blockages in the gases flow path in accordance with an embodiment of the invention.
Figure 11:
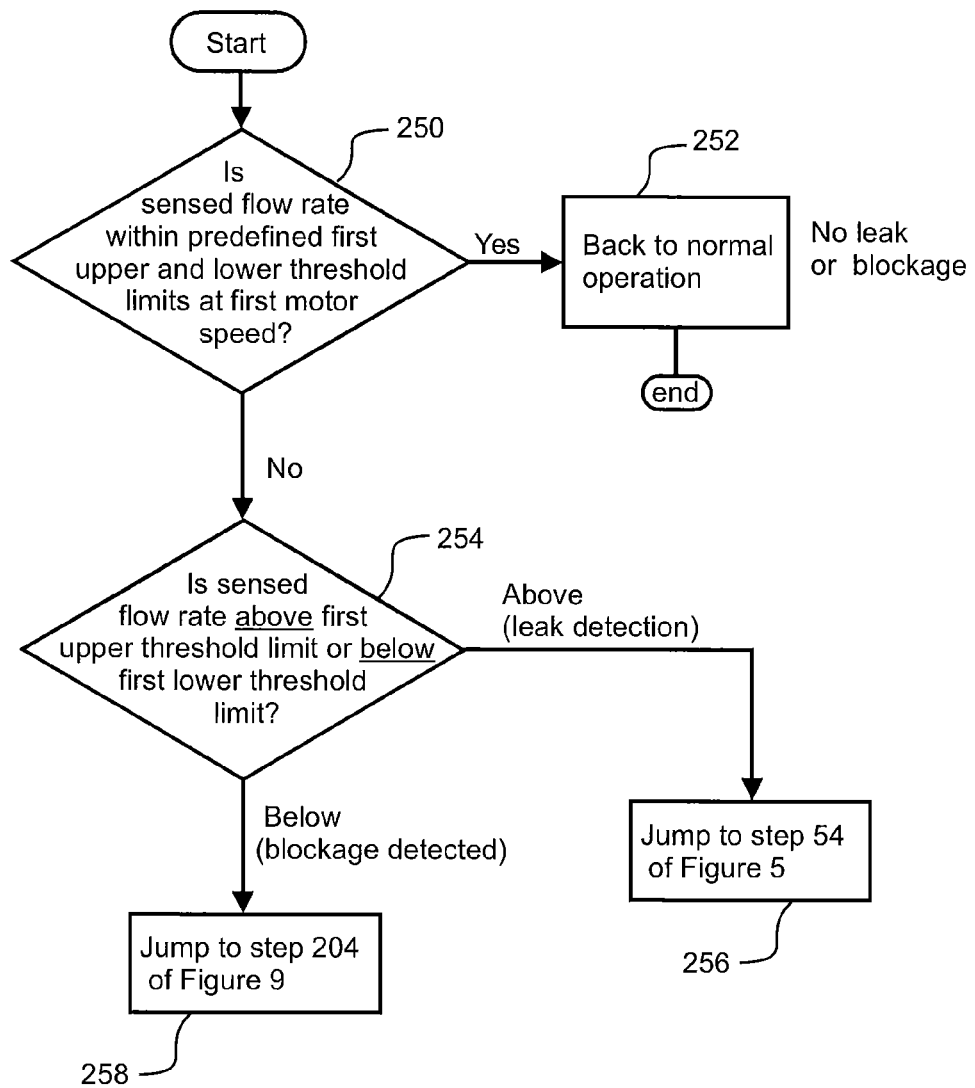
FIG. 11 is a flow diagram depicting the main steps of the fourth example of the flow path fault detection algorithm that is configured to detect both leaks and blockages in the gases flow path in accordance with an embodiment of the invention.

Referring to FIGS. 10 and 11, the combined leakage and blockage detection algorithm will be explained further. The process starts at 250 by determining whether the sensed flow rate is within the predefined first leak and blockage thresholds 220, 224, i.e. whether the sensed flow rate is within the shaded region indicated by 232 at any first motor speed in the first motor speed range 228. If the sensed flow rate is within the normal operating region 232, defined between the upper first leak threshold and lower first blockage threshold, then the algorithm reverts back to normal operation such that no leak or blockage is detected as indicated at 252. If a sensed flow rate falls outside the normal operating region 232 in the first motor speed range 228, then a decision is made on whether a possible leak or blockage has been detected. In particular, at step 254, it is determined whether the sensed flow rate is above the first leak threshold 220 in the leak detection region or below the first blockage threshold 224 in the blockage detection region.

If the sensed flow rate is in the leak detection region, the process moves to the leak detection process 256 which carries out the algorithm described with reference to FIG. 5, commencing at step 54. In particular, the process ramps the motor speed to the second motor speed range 230 and determines whether the sensed flow rate at the second higher motor speed exceeds the second leak threshold 222 such that a leak is detected and a warning signal generated, or otherwise modifies the first leak threshold and loops back to the start as previously described in relation to FIG. 5.

Alternatively, if the sensed flow rate is in the blockage detection region, the process moves to the blockage detection process 258 which carries out the algorithm described with reference to FIG. 9, commencing at step 204. In particular, the process ramps the motor speed to the second motor speed range 230 and determines whether the sensed flow at the second higher motor speed is below the second blockage threshold 226 such that a blockage is detected and a warning signal generated, or otherwise modifies the first blockage threshold and loops back to the start as described in relation to FIG. 9.

The foregoing description of the invention includes preferred forms thereof. Modifications may be made thereto, without departing from the scope of the invention as defined by the accompanying claims.

The invention claimed is:

1. A method for detecting a fault in a flow path of a respiratory assistance apparatus, the flow path comprising a motor-driven blower unit that is configured to generate a flow of gases and which is connected to a humidification unit that is configured to heat and humidify the flow of gases, comprising:
sensing a flow rate in the flow path at a first motor speed of the blower unit;
detecting the sensed flow rate is below a stored first threshold at the first motor speed;
increasing the motor speed of the blower unit to a second motor speed in response to detecting the sensed flow rate is below the first threshold, the second motor speed being higher than the first motor speed;
re-sensing the flow rate in the flow path at the second motor speed;
detecting the re-sensed flow rate at the second motor speed is at or above a stored second threshold; and
adjusting the first threshold by a predetermined level in response to detecting the re-sensed flow rate at the second motor speed is at or above the stored second threshold.

2. The method according to claim 1 wherein the first and second thresholds are configured for detecting a blockage in the flow path.

3. The method according to claim 1 wherein the first threshold has a higher probability of false alarm compared to the second threshold.

4. The method according to claim 1 wherein the first and second thresholds are extracted from respective stored threshold lines representing the flow rate threshold against motor speed for a predetermined motor speed range.

5. The method according to claim 1 wherein the first motor speed is within a first predetermined motor speed range and the second motor speed is within a predetermined second motor speed range.

6. The method according to claim 1 wherein the first motor speed is a current operating motor speed of the respiratory assistance apparatus.

7. The method according to claim 1 wherein the second motor speed is at or above 2000 rpm when the respiratory assistance apparatus is operating in an adult mode with an adult cannula.

8. The method according to claim 1 wherein the second motor speed is at least 6600 rpm when the respiratory assistance apparatus is operating in a junior mode with a pediatric cannula.

9. The method according to claim 1 wherein adjusting the first threshold comprises limiting the adjustment of the first threshold to not go below a predetermined stored lower limit level.

10. The method according to claim 1, wherein, in further response to detecting the re-sensed flow rate at the second motor speed is at or above the stored second threshold, resetting the motor speed to the first motor speed.

* * * * *